(12) United States Patent
Beauregard et al.

(10) Patent No.: US 11,512,062 B2
(45) Date of Patent: Nov. 29, 2022

(54) PROCESS FOR THE SYNTHESIS OF PIPERAZINYL-ETHOXY-BROMOPHENYL DERIVATES AND THEIR APPLICATION IN THE PRODUCTION OF COMPOUNDS CONTAINING THEM

(71) Applicant: LES LABORATOIRES SERVIER, Suresnes (FR)

(72) Inventors: Louis-Philippe Beauregard, Québec (CA); Martial Bertrand, Québec (CA); Pascall Giguere, Québec (CA); Christophe Hardouin, Sainte Adresse (FR); Bruno Schiavi, Gruchet le Valasse (FR)

(73) Assignee: LES LABORATOIRES SERVIER, Suresnes (FR)

( * ) Notice: Subject to any disclaimer, the term of this patent is extended or adjusted under 35 U.S.C. 154(b) by 0 days.

(21) Appl. No.: 17/283,107

(22) PCT Filed: Oct. 14, 2019

(86) PCT No.: PCT/EP2019/077729
§ 371 (c)(1),
(2) Date: Apr. 6, 2021

(87) PCT Pub. No.: WO2020/078875
PCT Pub. Date: Apr. 23, 2020

(65) Prior Publication Data
US 2021/0380549 A1  Dec. 9, 2021

(30) Foreign Application Priority Data
Oct. 15, 2018 (EP) .................................. 18306354

(51) Int. Cl.
*C07D 295/08* (2006.01)
*C07D 295/088* (2006.01)

(52) U.S. Cl.
CPC ................ *C07D 295/088* (2013.01)

(58) Field of Classification Search
CPC ................................................. C07D 295/088
See application file for complete search history.

(56) References Cited

FOREIGN PATENT DOCUMENTS

| EP | 2886545 | 6/2018 |
|---|---|---|
| WO | WO2015162515 | 10/2015 |
| WO | WO2016207226 | 12/2016 |

OTHER PUBLICATIONS

International Search Report for PCT/EP2019/077729 dated Jan. 31, 2020.
Maras, Nanad, et al., "Ring-opening reactions of 1,4-diarabicycle[2.2.2]octane (DABCO) derived quaternary ammonium salts with phenols and related nucleophiles", Organic & Biomolecular Chemistry, vol. 10, 2012, pp. 1300-1310.

*Primary Examiner* — Shawquia Jackson
(74) *Attorney, Agent, or Firm* — Hueschen and Sage

(57) ABSTRACT

Process for the industrial synthesis of the compound of formula (I):

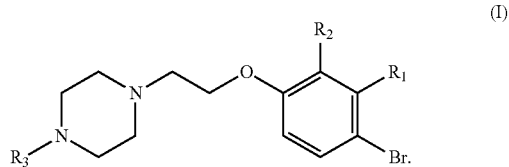

27 Claims, No Drawings

PROCESS FOR THE SYNTHESIS OF PIPERAZINYL-ETHOXY-BROMOPHENYL DERIVATES AND THEIR APPLICATION IN THE PRODUCTION OF COMPOUNDS CONTAINING THEM

The present invention relates to a new process for preparing piperazinyl-ethoxybromophenyl and piperazinyl-ethoxyphenylboronic acid derivatives and their application in the production of compounds containing them.

More specifically, the present invention relates to a new process for preparing 1-[2-(4-bromo-2-chloro-3-methylphenoxy)ethyl]-4-methylpiperazine and 1-{2-[2-chloro-3-methyl-4-(4,4,5,5-tetramethyl-1,3,2-dioxaborolan-2-yl)phenoxy]ethyl}-4-methylpiperazine and their application in the production of compounds containing them.

Even more specifically, the present invention relates to a new process for preparing 1-{2-[2-chloro-3-methyl-4-(4,4,5,5-tetramethyl-1,3,2-dioxaborolan-2-yl)phenoxy]ethyl}-4-methylpiperazine and its application in the production of 2-{[5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[1-(2,2,2-trifluoroethyl)-1H-pyrazol-5-yl]methoxy}phenyl)propanoic acid, referred to herein as 'Compound 1', and 2-{[5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid, referred to herein as 'Compound 2'.

Particularly, the present invention relates to a process for preparing a piperazinyl-ethoxybromophenyl compound of formula (I):

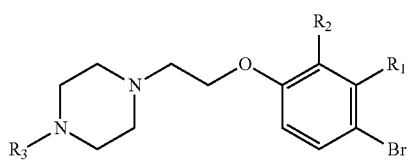

wherein:
R$_1$ and R$_2$ independently of one another represent a halogen atom, a linear or branched (C$_1$-C$_6$)alkyl group, a linear or branched (C$_1$-C$_6$)alkoxy group, a linear or branched (C$_1$-C$_6$)alkoxy(C$_1$-C$_6$)alkoxy group, a hydroxyl group or a cyano group,
R$_3$ represents a linear or branched (C$_1$-C$_6$)alkyl group.

Particularly, the present invention relates to a process for preparing a compound of formula (I) wherein:
R$_1$ and R$_2$ independently of one another represent a halogen atom or a linear or branched (C$_1$-C$_6$)alkyl group,
R$_3$ represents a linear or branched (C$_1$-C$_6$)alkyl group.

The present invention also relates to a process for preparing a piperazinyl-ethoxyphenylboronic acid compound of formula (II):

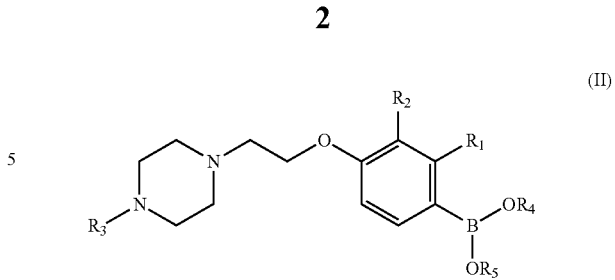

wherein:
R$_1$ and R$_2$ independently of one another represent a halogen atom, a linear or branched (C$_1$-C$_6$)alkyl group, a linear or branched (C$_1$-C$_6$)alkoxy group, a linear or branched (C$_1$-C$_6$)alkoxy(C$_1$-C$_6$)alkoxy group, a hydroxyl group or a cyano group,
R$_3$ represents a linear or branched (C$_1$-C$_6$)alkyl group,
R$_4$ and R$_5$ represent a hydrogen, a linear or branched (C$_1$-C$_6$)alkyl group, or R$_4$ and R$_5$ form with the oxygen atoms carrying them a ring which may be substituted by one to four linear or branched (C$_1$-C$_6$)alkyl group.

Particularly, the present invention relates to a process for preparing a compound of formula (II) wherein:
R$_1$ and R$_2$ independently of one another represent a halogen atom or a linear or branched (C$_1$-C$_6$)alkyl group,
R$_3$ represents a linear or branched (C$_1$-C$_6$)alkyl group,
R$_4$ and R$_5$ represent a hydrogen, a linear or branched (C$_1$-C$_6$)alkyl group, or R$_4$ and R$_5$ form with the oxygen atoms carrying them a ring which may be substituted by one to four linear or branched (C$_1$-C$_6$)alkyl group.

More particularly, the present invention relates to a process for preparing 1-{2-[2-chloro-3-methyl-4-(4,4,5,5-tetramethyl-1,3,2-dioxaborolan-2-yl)phenoxy]ethyl}-4-methylpiperazine of formula (III):

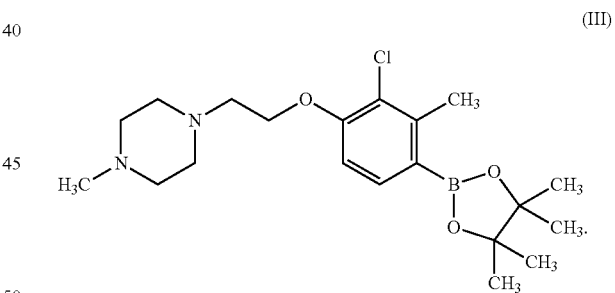

The compounds of formulae (I), (II) and (III) obtained according to the process of the invention are useful in the synthesis of Compound 1 or in the synthesis of Compound 2 as well as their structurally-close analogues.

Specifically, Compound 1 and Compound 2 have pro-apoptotic properties, notably, they are able to inhibit Mcl-1 protein, an anti-apoptotic Bcl-2 family member which is overexpressed in various types of cancer, making it possible to use Compound 1 and Compound 2 in pathologies involving a defect in apoptosis, such as, for example, in the treatment of cancer and of immune and auto-immune diseases.

In view of the pharmaceutical value of these compounds, it is important to be able to obtain them by an effective synthesis process that is readily transferable to the industrial scale and that results in Compound 1 or Compound 2 in a good yield and with excellent purity, starting from economical and readily obtainable starting materials.

The preparation of Compound 1 and its pharmacological effects on diverse cancer models are described in the literature (Kotschy et al. *Nature* 2016, 538, 477-482 and corresponding Supplementary Information, which is incorporated by reference). Moreover, Compound 1, Compound 2 and their structurally-close analogues, their preparation, their use as Mcl-1 inhibitors for the treatment of cancer and pharmaceutical formulations thereof, are described in WO 2015/097123. Particularly, the process for synthesizing compound of formula (III) is specifically disclosed in Preparation 5b of WO 2015/097123 in which compound of formula (III) is obtained in five steps starting from 4-bromo-2-chloro-phenol. Recently, CN 107573360 also discloses an alternative preparation of compound of formula (III) from 4-bromo-2-chloro-phenol in five steps. In addition, compound of formula (III) and its preparation are also specifically disclosed in WO 2016/207226, WO 2016/207217, WO 2016/207216 and WO 2017/125224. However, when transferred to the industrial scale, difficulties in implementing that process rapidly came to light: particularly, the risk of using highly inflammable and potential explosive reagents during protection step, the lack of selectivity during methylation reaction, and the weak yield and numerous byproducts during borylation and Mitsunobu reactions.

Moreover, an alternative process for synthesizing compounds of formula (II) is specifically disclosed in WO 2015/097123 in which compounds of formula (II) are obtained in three steps starting from 2,3-disubstituted-phenol. However, when transferred to the industrial scale, difficulties in implementing that process rapidly came to light too: particularly, weak yield during bromination step, weak yield and numerous byproducts during Mitsunobu reaction and weak yield during borylation step.

Consequently, the search for new efficient synthesis routes is still ongoing and the Applicant has continued his investigations to develop a new synthesis which yields compounds of formulae (I), (II) or (III) in reproducible manner, with excellent yields and without the need for laborious purification, with a purity which is compatible with its use as a pharmaceutically acceptable intermediate.

More especially, the Applicant has now developed a new synthesis process making it possible to obtain compounds of formulae (I) and (II) in reproducible manner without the need for laborious purification, using 1,2-disubstituted-3-bromophenyl derivatives as starting material. This new starting material has the advantage of being simple and readily obtainable in large amounts at less cost. Particularly, the Applicant has developed a new industrial synthesis process making it possible to obtain compounds of formula (III) in reproducible manner without the need for laborious purification, using 3-bromo-2-chlorotoluene as starting material. 3-Bromo-2-chlorotoluene has also the advantage of having in its structure a methyl group, which avoids incorporating a non-selective methylation step in the synthesis—a step which was problematic when transferred to the industrial scale.

The new process according to the invention has the advantage of using an efficient regioselective monobromination reaction, an outstanding ring-opening reaction of 1-alkyl-1-azoniabicyclo[2.2.2]octane compound and an efficacious borylation reaction. Bromination reaction of compound of formula (VI), particularly 2-fluoro-3-methyl-phenol, using N-bromosuccinimide (NBS) as reagent has been already disclosed in WO 2015/162515. However, it has been found that using NBS reagent provides undesired dibrominated by-products and lower yield. Ring-opening reaction of 1-alkyl-1-azoniabicyclo[2.2.2]octane compound has been already described in the literature (Maras et al. *Organic and Biomolecular Chemistry* 2012, 10, 1300-1310, which is incorporated by reference). However, the Applicant has found unexpected experimental conditions which are taught away by Maras publication.

A summary of the process according to the invention is showed in Scheme 1, vide infra.

Scheme 1

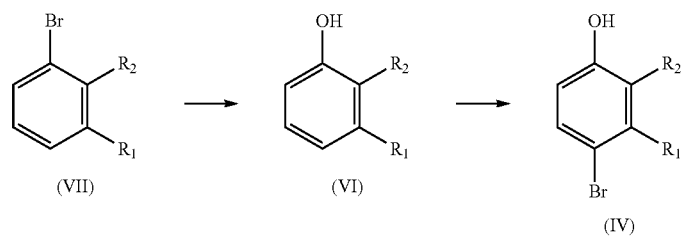

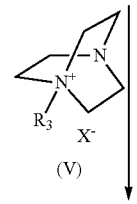

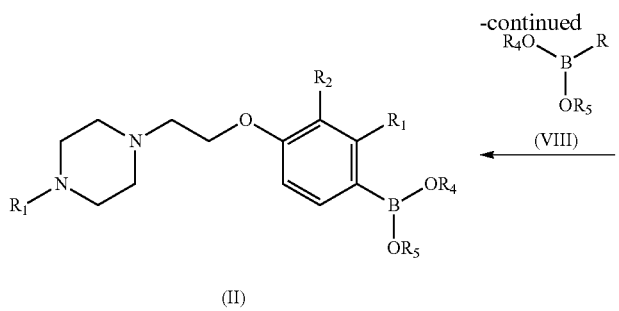

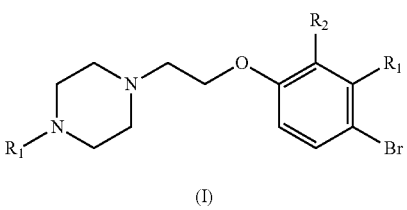

Ring-Opening Reaction of 1-alkyl-1-azoniabicyclo[2.2.2] octane Derivative: (IV)+(V)->(I)

A particular embodiment of the present invention relates to a process for preparing a compound of formula (I):

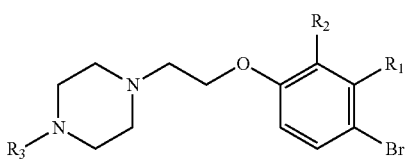

wherein:
  $R_1$ and $R_2$ independently of one another represent a halogen atom, a linear or branched $(C_1-C_6)$alkyl group, a linear or branched $(C_1-C_6)$alkoxy group, a linear or branched $(C_1-C_6)$alkoxy$(C_1-C_6)$alkoxy group, a hydroxyl group or a cyano group.
  $R_3$ represents a linear or branched $(C_1-C_6)$alkyl group.
comprising the step of reacting a compound of formula (IV):

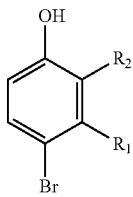

wherein $R_1$ and $R_2$ are as defined before,
with a compound of formula (V):

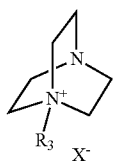

wherein $R_3$ is as defined before, and $X^-$ represents a monovalent anionic counter-ion,
in a solvent, at high temperature in the presence of a base.

In one embodiment, solvent that may be used to carry out the conversion of the compound of formula (IV) to form the compound of formula (I) is preferably a polar aprotic solvent. Among the polar aprotic solvents that may be used to carry out the conversion of the compound of formula (IV) to form the compound of formula (I), there may be mentioned, without implying any limitation, anisole, pyridine, N-methyl-2-pyrrolidone, N,N-dimethylformamide, N,N-dimethylacetamide, diglyme, dimethyl sulfoxide, acetonitrile, tetrahydrofuran, 2-methyltetrahydrofuran, polyethylene glycol, sulfolane . . . .

The solvent used to carry out the conversion of the compound of formula (IV) to form the compound of formula (I) may also be composed of a mixture of two or more solvents from among the afore-mentioned solvents.

The solvent preferably used to carry out the conversion of the compound of formula (IV) to form the compound of formula (I) is anisole.

Preferably, the reaction converting the compound of formula (IV) into the compound of formula (I) is carried out at a temperature superior to 135° C., more preferably between 140° C. and 150° C. One advantageous embodiment for the conversion of the compound of formula (IV) into the compound of formula (I) is to carry out the reaction between 135° C. and 145° C. One other advantageous embodiment for the conversion of the compound of formula (IV) into the compound of formula (I) is to carry out the reaction at 140° C.

Among the base that may be used to carry out the conversion of the compound of formula (IV) to form the compound of formula (I), there may be mentioned, without implying any limitation, potassium tert-butoxide, lithium tert-butoxide, potassium acetate, lithium ethoxide, carbonate salts such as cesium carbonate, potassium carbonate, sodium carbonate, lithium carbonate . . . .

The base preferably used to carry out the conversion of the compound of formula (IV) to form the compound of formula (I) is a carbonate salt, more preferably cesium carbonate.

The compound of formula (I) can be isolated as a freebase, a monohydrohalide salt or a dihydrohalide salt. Preferably, the compound of formula (I) can be isolated as a monohydrohalide salt or a dihydrohalide salt. More preferably, the compound of formula (I) is isolated as a dihydrohalide salt, even more preferably as a dihydrochloride salt.

The isolation of compound of formula (I) as a monohydrohalide salt is preferably performed in tert-butyl methyl ether, dioxane, toluene, cyclohexane, cycloheptylmethyl ether or ethyl acetate, more preferably in tert-butyl methyl ether.

The isolation of compound of formula (I) as a dihydrohalide salt is preferably performed in water.

Compound of formula (V) is obtained from 1,4-diazabicyclo[2.2.2]octane (also known as DABCO; CAS Number: 280-57-9). Compound of formula (V) can be synthesized by reacting 1,4-diazabicyclo[2.2.2]octane with an alkylating agent selected from alkyl halide, alkyl tosylate, alkyl sulphate or alkyl mesylate. Particularly, compound of formula (V) is defined as follows:

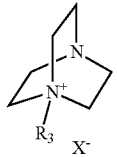

(V)

wherein $R_3$ is as defined before, and $X^-$ represents a monovalent anionic counter-ion selected from halide, tosylate, sulphate or mesylate.

Advantageously, compound of formula (V) is defined as follows:

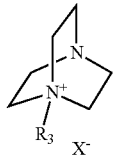

(V)

wherein $R_3$ represents a methyl group and $X^-$ represents a tosylate counter-ion.

Preferably, compound of formula (V) can be synthesized with a methylating agent selected from methyl halide, methyl tosylate (also known as 4-methylbenzene-1-sulfonate), methyl sulphate or methyl mesylate, more preferably methyl tosylate.

Compound of formula (V) can be synthesized separately or in situ, preferably in situ.

In a particular embodiment, compound of formula (I) is obtained by using 1,4-diazabicyclo[2.2.2]octane.

Regioselective Monobromination Reaction: (VI)->(IV)

A particular embodiment of the present invention relates to a process wherein the compound of formula (IV):

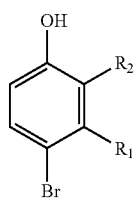

(IV)

wherein $R_1$ and $R_2$ independently of one another represent a halogen atom, a linear or branched $(C_1-C_6)$alkyl group, a linear or branched $(C_1-C_6)$alkoxy group, a linear or branched $(C_1-C_6)$alkoxy$(C_1-C_6)$alkoxy group, a hydroxyl group or a cyano group, is obtained by a regioselective monobromination reaction of a compound of formula (VI):

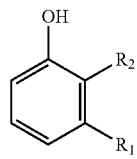

(VI)

wherein $R_1$ and $R_2$ are as defined before,
in a solvent in the presence of a brominating agent.

In the process according to the invention, the reaction converting the compound of formula (VI) into the compound of formula (IV) is carried out in the presence of 1 equivalent of brominating agent.

Among the brominating agents that may be used to carry out the conversion of the compound of formula (VI) to form the compound of formula (IV), there may be mentioned, without implying any limitation, N-bromosuccinimide, bromine, sodium bromide/trichloroisocyanuric acid, bromine/sodium acetate, bromotrichloromethane, 1,2-dibromo-1,1,2,2-tetrachloroethane, tetrabromomethane, carbon tetrabromide, tetrabutylammonium tribromide, trimethylphenylammonium tribromide, benzyltrimethylammonium tribromide, pyridinium bromide perbromide, 4-dimethylaminopyridinium bromide perbromide, 1-butyl-3-methylimidazolium tribromide, 1,8-diazabicyclo[5.4.0]-7-undecene hydrogen tribromide, N-bromophthalimide, N-bromosaccharin, N-bromoacetamide, 2-bromo-2-cyano-N,N-dimethylacetamide, 1,3-dibromo-5,5-dimethylhydantoin, dibromoisocyanuric acid, monosodium bromoisocyanurate hydrate, boron tribromide (17% in dichloromethane, ca. 1 mol/L), boron tribromide (29% in heptane, ca. 1 mol/L), phosphorus tribromide, bromodimethylsulfonium bromide, 5,5-dibromomeldrum's acid, 2,4,4,6-tetrabromo-2,5-cyclohexadienone, bis(2,4,6-trimethylpyridine)-bromonium hexafluorophosphate . . . .

The brominating agent preferably used to carry out the conversion of the compound of formula (VI) to form the compound of formula (IV) is N-bromosuccinimide, bromine, sodium bromide/trichloroisocyanuric acid or bromine/sodium acetate, more preferably bromine, sodium bromide/trichloroisocyanuric acid or bromine/sodium acetate, even more preferably, bromine.

Among the solvents that may be used to carry out the conversion of the compound of formula (VI) to form the compound of formula (IV), there may be mentioned, without implying any limitation, dichloromethane, 1,2-dichloroethane, tetrahydrofuran, acetonitrile, acetone, dimethylformamide, water, methanol, acetic acid, sulfuric acid, hydrobromic acid . . . .

The solvent used to carry out the conversion of the compound of formula (VI) to form the compound of formula (IV) may also be composed of a mixture of two or more solvents from among the afore-mentioned organic solvents.

The solvent preferably used to carry out the conversion of the compound of formula (VI) to form the compound of formula (IV) is acetic acid, dichloromethane, a mixture of methanol and sulfuric acid, or a mixture of acetic acid and dichloromethane. In a preferred embodiment, the solvent used to carry out the conversion of the compound of formula (VI) to form the compound of formula (IV) is a mixture of acetic acid and dichloromethane, more preferably a mixture from 10% v/v to 100% v/v acetic acid in dichloromethane, even more preferably, a mixture from 15% v/v to 30% v/v acetic acid in dichloromethane. Advantageously, the solvent used to carry out the conversion of the compound of formula (VI) to form the compound of formula (IV) is a mixture of 25% v/v acetic acid and dichloromethane Preferably, the reaction converting the compound of formula (VI) into the compound of formula (IV) is carried out between −20° C. and 30° C., more preferably between −15° C. and 5° C., even more preferably between −15° C. and −5° C. In other preferred embodiment, the reaction converting the compound of formula (VI) into the compound of formula (IV) is carried out between −5° C. and 5° C.

Preferably, the bromination reaction can be conducted by diluting the compound of formula (VI) with about 10 to about 20, more preferably from about 10 to about 15, even more preferably about 10, volumes of organic solvents or mixtures of organic solvents.

Hydroxylation Reaction: (VII)->(VI)

A particular embodiment of the present invention relates to a process wherein the compound of formula (VI):

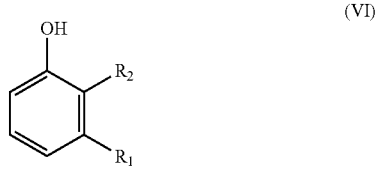

(VI)

wherein $R_1$ and $R_2$ independently of one another represent a halogen atom, a linear or branched $(C_1-C_6)$alkyl group, a linear or branched $(C_1-C_6)$alkoxy group, a linear or branched $(C_1-C_6)$alkoxy$(C_1-C_6)$alkoxy group, a hydroxyl group or a cyano group,
is obtained by a hydroxylation reaction of a compound of formula (VII):

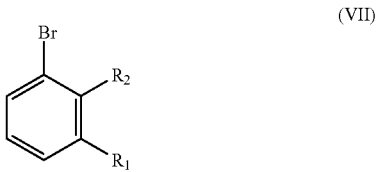

(VII)

wherein $R_1$ and $R_2$ are as defined before,
in a solvent in the presence of a metal transition complex and a base.

In the process according to the invention, the reaction converting the compound of formula (VII) into the compound of formula (VI) can be carried out by various metal-catalyzed hydroxylation reactions (Maleczka et al., *J. Am. Chem. Soc.* 2003, 125, 7792-7793; Willis, *Angew. Chem. Int. Ed.* 2007, 46, 3402-3404; Alonso et al., *Chem. Eur. J.* 2010, 16, 5274-5284; Enthaler et al., *Chem. Soc. Rev.* 2011, 40, 4912-4924; Xia et al., *J. Am. Chem. Soc.* 2016, 138, 13493-13496, which are incorporated by reference). Advantageously, in the process according to the invention, the reaction converting the compound of formula (VII) into the compound of formula (VI) can be carried out in the presence of metal transition complex which is a palladium complex comprising a palladium catalyst and a ligand.

Among the palladium catalysts that may be used to carry out the conversion of the compound of formula (VII) to form the compound of formula (VI), there may be mentioned, without implying any limitation, tris(dibenzylideneacetone) dipalladium $Pd_2(dba)_3$, palladium(II) acetate $Pd(OAc)_2$, palladium on carbon Pd/C, tetrakis(triphenylphosphine)palladium $Pd(PPh_3)_4$ . . . .

The palladium catalyst preferably used to carry out the conversion of the compound of formula (VII) to form the compound of formula (VI) is $Pd_2(dba)_3$.

Among the ligands that may be used to carry out the conversion of the compound of formula (VII) to form the compound of formula (VI), there may be mentioned, without implying any limitation, 2-dicyclohexylphosphino-2',4',6'-triisopropylbiphenyl XPhos, 2-di-tert-butylphosphino-2',4',6'-triisopropylbiphenyl t-BuXPhos . . . .

The ligand preferably used to carry out the conversion of the compound of formula (VII) to form the compound of formula (VI) is t-BuXPhos.

In the process according to the invention, the reaction converting the compound of formula (VII) into the compound of formula (VI) is carried out in the presence of at least 0.01 equivalent of palladium catalyst, more preferably at least 0.0075 equivalent. The reaction converting the compound of formula (VII) into the compound of formula (VI) is carried out in the presence of at least 0.03 equivalent of ligand, more preferably at least 0.02 equivalent. Advantageously, the reaction converting the compound of formula (VII) into the compound of formula (VI) is carried out in the presence of at least 0.01 equivalent of palladium catalyst and of at least 0.03 equivalent of ligand. More advantageously, the reaction converting the compound of formula (VII) into the compound of formula (VI) is carried out in the presence of 0.01 equivalent of palladium catalyst and 0.04 equivalent of ligand.

Among the bases that may be used to carry out the conversion of the compound of formula (VII) to form the compound of formula (VI), there may be mentioned, without implying any limitation, potassium acetate, sodium tert-butoxide, sodium bicarbonate, potassium carbonate, hydroxide salts such as potassium hydroxide, sodium hydroxide, cesium hydroxide, lithium hydroxide . . . .

The base preferably used to carry out the conversion of the compound of formula (VII) to form the compound of formula (VI) is a hydroxide salt, more preferably potassium hydroxide, sodium hydroxide, cesium hydroxide, lithium hydroxide, even more preferably potassium hydroxide.

Among the solvents that may be used to carry out the conversion of the compound of formula (VII) to form the compound of formula (VI), there may be mentioned, without implying any limitation, 1,4-dioxane, cyclopentyl methyl ether, toluene, heptane, water, acetonitrile, dimethylsulfoxide, N,N-dimethylformamide, N-methyl-2-pyrrolidone, N,N-dimethylacetamide, tetrahydrofuran, 2-methyltetrahydrofuran, tert-butyl methyl ether . . . .

The solvent used to carry out the conversion of the compound of formula (VII) to form the compound of formula (VI) may also be composed of a mixture of two or more solvents from among the afore-mentioned organic solvents, or a mixture of water and a solvent from among the afore-mentioned organic solvents.

The solvent preferably used to carry out the conversion of the compound of formula (VII) to form the compound of formula (VI) is 1,4-dioxane or a mixture of water and 1,4-dioxane, more preferably a mixture or water and 1,4-dioxane. Advantageously, the proportion of 1,4-dioxane in water is at least 5%, more preferably at least 15%, even more preferably at least 25%.

An advantageous embodiment relates to the sequence of hydroxylation and regioselective monobromination reactions converting the compound of formula (VII) into the compound of formula (IV) without isolating compound of formula (VI). During such advantageous embodiment, the organic solvent used to carry out the conversion of the non-isolated compound of formula (VI) into the compound of formula (IV) is composed of a mixture of solvents, preferably, a mixture of 1,4-dioxane, acetic acid and dichloromethane, wherein 1,4-dioxane is the residual solvent coming from the said hydroxylation step (i.e. the conversion step of compound of formula (VII) into the compound of formula (VI)).

Borylation Reaction: (I)->(II)

A particular embodiment of the present invention relates to a process for preparing a compound of formula (II):

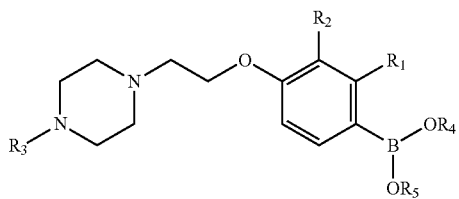

(II)

wherein:
- $R_1$ and $R_2$ independently of one another represent a halogen atom, a linear or branched $(C_1-C_6)$alkyl group, a linear or branched $(C_1-C_6)$alkoxy group, a linear or branched $(C_1-C_6)$alkoxy$(C_1-C_6)$alkoxy group, a hydroxyl group or a cyano group,
- $R_3$ represents a linear or branched $(C_1-C_6)$alkyl group,
- $R_4$ and $R_5$ represent a hydrogen, a linear or branched $(C_1-C_6)$alkyl group, or $R_4$ and $R_5$ form with the oxygen atoms carrying them a ring which may be substituted by one to four linear or branched $(C_1-C_6)$alkyl group, comprising the step of reacting a compound of formula (I), (I)

wherein $R_1$, $R_2$ and $R_3$ are as defined before, with a boronic ester of formula (VIII):

(VIII)

wherein $R_4$ and $R_5$ are as defined before and R represents a hydrogen atom, a hydroxy group, a linear or branched $(C_1-C_6)$alkoxy group, or a $(C_0-C_6)$alkyl-B$(OR_4)(OR_5)$ group.

In the process according to the invention, conversion of the compound of formula (I) into the compound of formula (II) consists of the action of a compound of formula (VIII) wherein R represents a hydrogen atom, a hydroxy group, or a linear or branched $(C_1-C_6)$alkoxy group, in an organic solvent or a mixture of organic solvents in the presence of a base. Advantageously, the reaction converting the compound of formula (I) into the compound of formula (II) is carried out in tetrahydrofuran or 2-methyltetrahydrofuran, more preferably 2-methyltetrahydrofuran. Preferably, the reaction converting the compound of formula (I) into the compound of formula (II) is carried out in the presence of n-butyllithium.

Alternatively, in the process according to the invention, conversion of the compound of formula (I) into the compound of formula (II) consists of the action of a compound of formula (VIII) wherein R represents a $(C_0-C_6)$alkyl-B$(OR_4)(OR_5)$ group, in an organic solvent or a mixture of organic solvents in the presence of a base and a palladium complex (Miyaura borylation). Advantageously, the said palladium complex is bis(triphenylphosphine)palladium(II) dichloride Pd(PPh$_3$)$_2$Cl$_2$.

The compound of formula (I) is preferably used as a freebase for its conversion into the compound of formula (II). When the compound of formula (I) is a dihydrohalide salt, two supplementary equivalents of the said base are advantageously added in the reaction mixture to carry out the conversion of the compound of formula (I) to form the compound of formula (II).

To carry out the conversion of the compound of formula (I) to form the compound of formula (II), compound of formula (I) is advantageously obtained from the reaction of compound of formula (IV) with compound of formula (V).

Advantageously, the present invention relates to a process for preparing a compound of formula (II):

(II)

wherein:
- $R_1$ and $R_2$ independently of one another represent a halogen atom, a linear or branched $(C_1-C_6)$alkyl group, a linear or branched $(C_1-C_6)$alkoxy group, a linear or branched $(C_1-C_6)$alkoxy$(C_1-C_6)$alkoxy group, a hydroxyl group or a cyano group,
- $R_3$ represents a linear or branched $(C_1-C_6)$alkyl group,
- $R_4$ and $R_5$ represent a hydrogen, a linear or branched $(C_1-C_6)$alkyl group, or $R_4$ and $R_5$ form with the oxygen atoms carrying them a ring which may be substituted by one to four linear or branched $(C_1-C_6)$alkyl group, characterized in that compound of formula (VII):

(VII)

wherein $R_1$ and $R_2$ are as defined before, is subjected to a hydroxylation reaction in the presence of a metal transition complex and a base in a solvent, to yield the compound of formula (VI):

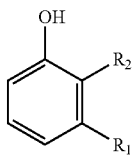

wherein $R_1$ and $R_2$ are as defined before,
which compound of formula (VI) is subjected to a regioselective monobromination reaction in the presence of a brominating agent in a solvent,
to yield the compound of formula (IV):

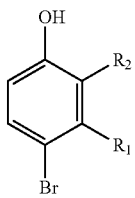

wherein $R_1$ and $R_2$ are as defined before,
which compound of formula (IV) is reacted in a solvent at high temperature in the presence of a base and a compound of formula (V):

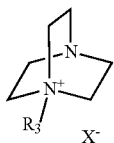

wherein $R_3$ is as defined before, and $X^-$ represents a monovalent anionic counter-ion,
to yield the compound of formula (I):

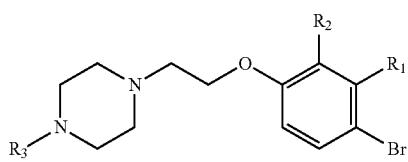

wherein $R_1$, $R_2$ and $R_3$ are as defined before,
which compound of formula (I) undergoes a borylation reaction in the presence of a boronic ester of formula (VIII):

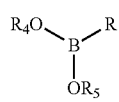

wherein $R_4$ and $R_5$ are as defined for formula (II) and R represents a hydrogen atom, a hydroxy group, a linear or branched $(C_1\text{-}C_6)$alkoxy group, or a $(C_0\text{-}C_6)$alkyl-$B(OR_4)(OR_5)$ group,
to yield the compound of formula (II).

In a specific embodiment, $R_1$ preferably represents a halogen atom or a linear or branched $(C_1\text{-}C_6)$alkyl group, more preferably a fluorine atom, a chlorine atom, a ethyl group or a methyl group, even more preferably a methyl group. $R_2$ represents advantageously a halogen atom or a linear or branched $(C_1\text{-}C_6)$alkyl group, more advantageously a chlorine atom or a in methyl group, even more advantageously a chlorine atom. Particularly, $R_3$ represents a methyl group. More particularly, $R_1$ represents a linear or branched $(C_1\text{-}C_6)$alkyl group, $R_2$ represents a halogen atom and $R_3$ represents a methyl group. Even more particularly, $R_1$ and $R_3$ represent a methyl group and $R_2$ represents a chlorine atom. Preferably, $R_4$ and $R_5$ form with the oxygen atoms carrying them a ring which can be a dioxaboretane, a dioxaborolane, a dioxaborinane, or a dioxaborepane, more preferably a dioxaborolane ring. Advantageously, $R_4$ and $R_5$ form with the oxygen atoms carrying them a ring which may be substituted by one to four linear or branched $(C_1\text{-}C_6)$alkyl group. More advantageously, $R_4$ and $R_5$ form with the oxygen atoms carrying them a 4,4,5,5-tetramethyl-1,3,2-dioxaborolan-2-yl ring.

Advantageously, the present invention relates to a process for preparing a compound of formula (III):

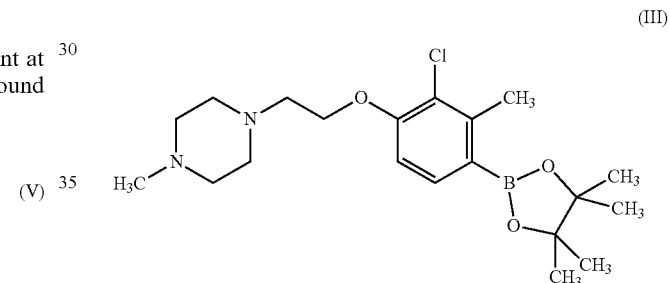

characterized in that compound of formula (VII):

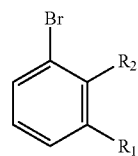

wherein $R_1$ represents a methyl group and $R_2$ represents a chlorine atom,
is subjected to a hydroxylation reaction in the presence of a metal transition complex and a base in a solvent,
to yield the compound of formula (VI):

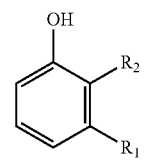

wherein $R_1$ and $R_2$ are as defined before, which compound of formula (VI) is subjected to a regioselective monobromination reaction in the presence of a brominating agent in a solvent,
to yield the compound of formula (IV):

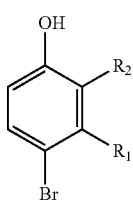

(IV)

wherein R$_1$ and R$_2$ are as defined before,
which compound of formula (IV) is reacted in a solvent at high temperature in the presence of a base and a compound of formula (V):

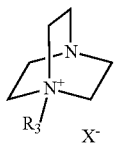

(V)

wherein R$_3$ represents a methyl group and X$^-$ represents a monovalent anionic counter-ion,
to yield the compound of formula (I):

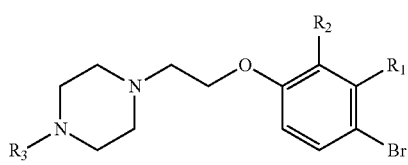

(I)

wherein R$_1$, R$_2$ and R$_3$ are as defined before,
which compound of formula (I) undergoes a borylation reaction in the presence of a boronic ester of formula (VIII):

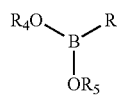

(VIII)

wherein R$_4$ and R$_5$ form with the oxygen atoms carrying them a 4,4,5,5-tetramethyl-1,3,2-dioxaborolan-2-yl ring and R represents a hydrogen atom, a hydroxy group, a linear or branched (C$_1$-C$_6$)alkoxy group, or a (C$_0$-C$_6$)alkyl-B(OR$_4$)(OR$_5$) group,
to yield the compound of formula (III).

The compound of formula (V), (VII) and (VIII) are commercially available or readily obtainable by the skilled person using chemical reactions that are customary or described in the literature.

The present process is especially advantageous for the following reasons:
it makes it possible to obtain the compound of formula (I), on the industrial scale in excellent yields starting from a simple and low-cost starting material without the need for laborious purification;
it makes it possible to obtain the compound of formula (II), more particularly compound of formula (III), on the industrial scale in excellent yields starting from a simple and low-cost starting material without the need for laborious purification;
it makes it possible to avoid volatile intermediates as well as the use of highly inflammable and potential explosive reagents;
it makes it possible to achieve high levels of purity using standard crystallization techniques.

The present invention also relates to the use of the compound of formula (VII) for the synthesis of compound of formula (I) or compound of formula (II). Alternatively, the present invention also relates to the use of the compound of formula (VII) wherein R$_1$ represents a methyl group and R$_2$ represents a chlorine atom for the synthesis of Compound 1 or Compound 2.

The present invention also relates to the use of the compound of formula (V) for the synthesis of compound of formula (I) or compound of formula (II). Alternatively, the present invention also relates to the use of the compound of formula (V) wherein R$_3$ represents a methyl group for the synthesis of Compound 1 or Compound 2.

The compound of formula (II) or the compound of formula (III) hereby obtained are subsequently subjected to a series of customary chemical reactions, such as described in WO 2015/097123, to yield Compound 1 or Compound 2 as well as their structurally-close analogues. Advantageously, compound of formula (III), obtained according to the present invention, can be used in a cross-coupling reaction, such as a Suzuki-type cross-coupling reaction, for the preparation of Compound 1 or Compound 2.

Advantageously, Compound 1 or Compound 2 are obtained by using 1,4-diazabicyclo[2.2.2]octane during the process for the preparation of compound of formula (II) or compound of formula (III).

In order to properly validate the reaction routes, the synthesis intermediates were systematically isolated and characterized. However, it is possible to considerably optimize the procedures by limiting the number of intermediates isolated.

Preferably, the reactants are agitated during the reaction period using suitable mechanical agitators or stirrers. The reactions can be conducted from about 2 to about 24 hours or more, depending on the temperatures, dilution volumes, catalysts, concentrations and/or nature of the materials in the reaction mixtures. The term 'about' as used herein means +/−5%, in particular +/−2%, more particularly +/−1%.

The structures of the compounds described were confirmed by the usual spectroscopic techniques. For example, $^1$H NMR data is in the form of delta values, given in part per million (ppm), using the residual peak of the solvent (7.26 ppm for CDCl$_3$) as internal standard. Splitting patterns are designated as: s (singlet), d (doublet), t (triplet), m (multiplet), br or brs (broad singlet).

The Examples herein below illustrate the invention but do not limit it in any way.

EXAMPLE 1: PREPARATION OF 2-CHLORO-3-METHYLPHENOL (HYDROXYLATION REACTION)

A solution of 1-bromo-2-chloro-3-methylbenzene (5.00 g; 24.33 mmol) in dioxane (12.5 mL) and a solution of potassium hydroxide (2.25 g; 40.14 mmol) in water (12.5 mL)

were degassed with nitrogen for 15 minutes. The solutions were combined. t-BuXPhos (827 mg; 1.95 mmol) and Pd$_2$(dba$_3$) (446 mg; 0.48 mmol) were added and the reaction mixture was heated in a sealed tube at 100° C. for 35 minutes. The reaction mixture was cooled to 20° C. and washed with tert-butyl methyl ether. The aqueous phase was back extracted with a 1 N NaOH solution, acidified to pH 4 with a 3 N hydrochloric acid solution and extracted with dichloromethane. The combined organic phases were dried over sodium sulfate, filtered and concentrated to provide the title compound as a pale yellow solid (2.8 g, 80% yield).

$^1$H NMR (400 MHz, CDCl$_3$): δ ppm 6.97-7.11 (m, 1H); 6.73-6.90 (m, 2H); 5.88 (brs, 1H); 2.37 (s, 3H)

EXAMPLE 2: PREPARATION OF 4-BROMO-2-CHLORO-3-METHYLPHENOL (REGIOSELECTIVE MONOBROMINATION REACTION)

A solution of bromine (1089 g; 6.82 mol) in dichloromethane (1.94 L; 2 vol.) was added at 0° C. to a solution of 2-chloro-3-methylphenol (972 g; 6.82 mol), which can be obtained as described in Example 1 above, in a mixture of dichloromethane (5.35 L; 5.5 vol.) and acetic acid (2.43 L; 2.5 vol.). After stirring for 15 minutes at 0° C., the reaction mixture was warmed at room temperature and was washed with water and with a 5% KHCO$_3$ solution then dried over sodium sulfate. After filtration, the product was obtained by concentration to dryness and was carried as is in the next step (1.44 kg; 95%).

$^1$H NMR (400 MHz, CDCl$_3$): δ ppm 7.35 (d, J=8.8 Hz, 1H); 6.78 (d, J=8.6 Hz, 1H); 5.64 (brs, 1H); 2.49 (s, 3H)

$^{13}$C NMR (101 MHz, CDCl$_3$): δ ppm 150.7, 135.9, 131.2, 121.1, 115.3, 114.5, 20.8 LC-MS [ESI$^-$] m/z: 219.0, 219.8 [M+H]$^+$

EXAMPLE 3: PREPARATION OF 4-BROMO-2-CHLORO-3-METHYLPHENOL (REGIOSELECTIVE MONOBROMINATION REACTION—OTHER CONDITIONS)

A solution of brominating agent (1 eq.) in solvent was added at 0° C. to a solution of 2-chloro-3-methylphenol (100 mg) in solvent. After stirring for 15 minutes at 0° C., the reaction mixture was washed with water and with a 5% KHCO$_3$ solution then dried over sodium sulfate. After filtration, the product was obtained by concentration to dryness and was carried as is in the next step. The structure of the expected product was confirmed by $^1$H NMR and delta values are the same as the one found for Example 2 above.

TABLE 1

Experimental conditions used for the preparation of 4-bromo-2-chloro-3-methylphenol

| Entry | Brominating agent | Solvent | Dilution (vol) | Yield |
|---|---|---|---|---|
| 1 | N-bromosuccinimide | methanol + sulfuric acid | 15 | 78% |
| 2 | bromine | acetic acid | 15 | 89% |
| 3 | bromine | dichloromethane | 15 | 83% |
| 4 | bromine | acetic acid 25% v/v in dichloromethane | 15 | 88% |
| 5 | bromine | acetic acid 25% v/v in dichloromethane | 10 | 92% |

EXAMPLE 4: PREPARATION OF 4-BROMO-2-CHLORO-3-METHYLPHENOL (ONE-POT HYDROXYLATION AND REGIOSELECTIVE MONOBROMINATION REACTIONS)

A solution of 1-bromo-2-chloro-3-methylbenzene (354 g; 1.72 mol) and potassium hydroxide (242 g; 4.30 mol) in 1,4-dioxane (710 mL; 2.0 vol.) and water (2150 mL; 6.0 vol.) was degassed, under stirring, with nitrogen for 15 minutes. t-BuXphos (29.2 g; 0.069 mol) and Pd$_2$(dba)$_3$ (15.8 g; 0.017 mol) were added and the suspension was heated to reflux (90-95° C.) for 60 minutes. Reaction completion was confirmed by HPLC. The resulting suspension was cooled to 20-25° C. tert-Butyl methyl ether (800 mL) was added and the biphasic mixture was stirred for 10-15 minutes. The catalyst residue was removed by filtration over a pad of Celite and the cake was rinsed with tert-butyl methyl ether and 1 N potassium hydroxide solution. The aqueous phase was washed three times with tert-butyl methyl ether then was acidified to pH 1-2 with 12 N hydrochloric acid solution. The solution was extracted three times with dichloromethane then the volume of the solution was adjusted (1153 mL; 5.0 vol. relative to the phenol) with dichloromethane in order to telescope at the appropriate concentration with the next step. The concentration of 2-chloro-3-methylphenol in the solution was determined by quantitative GC-FID analysis (128.1 mg/mL; 230.6 g; 1.617 mol.).

The solution of 2-chloro-3-methylphenol was charged to a 5.0 L reactor and acetic acid (584 mL; 2.5 vol. relative to the phenol) was added. The solution was then cooled to −10° C./−15° C. under nitrogen and a solution of bromine (258.5 g; 1.617 mol) in dichloromethane (477 mL; 2.1 vol. relative to the phenol) was added in 70 minutes between −13° C. and −7° C. Additional bromine (3.5 g; 0.022 mol) in dichloromethane (20 mL; 0.06 vol.) was added. Water (1.4 L) was added in 10 minutes between −11° C. and 2° C. The solution was warmed to 20-25° C. and sodium bisulfite (50 g; 0.48 mol) was added. The solution was stirred for 15-20 minutes. Phases were separated and then the aqueous phase was extracted with dichloromethane. Pooled organic phases were washed twice with water, twice with 10% potassium bicarbonate solution and brine. The solution was dried over magnesium sulfate. The cake was washed with dichloromethane. Solvents were evaporated under vacuum and residual 1,4-dioxane was azeotroped with heptanes to give the product of the title as a pale brown solid (353 g, crude yield: 92.6%).

$^1$H NMR (400 MHz, CDCl$_3$): δ ppm 7.35 (d, J=8.8 Hz, 1H); 6.78 (d, J=8.6 Hz, 1H); 5.64 (brs, 1H); 2.49 (s, 3H)

$^{13}$C NMR (101 MHz, CDCl$_3$): δ ppm 150.7, 135.9, 131.2, 121.1, 115.3, 114.5, 20.8 LC-MS [ESI$^-$] m/z: 219.0, 219.8 [M+H]$^+$

EXAMPLE 5: PREPARATION OF 1-[2-(4-BROMO-2-CHLORO-3-METHYLPHENOXY) ETHYL]-4-METHYLPIPERAZINE (RING-OPENING OF 1-ALKYL-1-AZONIABICYCLO[2.2.2] OCTANE)

A solution of methyl 4-methylbenzene-1-sulfonate (592 g; 3.18 mol) in anisole (320 mL) was added over 15 minutes to a solution of 1,4-diazabicyclo[2.2.2]octane (389 g; 3.47 mol) in anisole (6.4 L). After stirring for 1 hour at 70° C., under vigorous agitation, Cs$_2$CO$_3$ (1130 g; 3.466 mol) was added portion wise over 5 minutes. A solution of 4-bromo-2-chloro-3-methylphenol (640 g; 2.89 mol), obtained as described in Examples 2 or 3 above, in anisole (0.64 L) was added over 10 minutes. The reaction mixture was stirred for 6 hours at 140° C. After cooling to room temperature, tert-butyl methyl ether and ethyl acetate were added and the mixture was washed with water and brine, dried with sodium sulfate and the resulting product solution was kept for the next step.

A mixture of tert-butyl methyl ether (1.28 L) and ethanol (219 mL; 3.75 mol) was added over 30 minutes to a solution of acetyl chloride (272 g; 3.46 mol) keeping the temperature mixture below 25° C. After stirring for 30 minutes, the resulting solution was added to the organic phase obtained above over 1 hour at room temperature. After stirring the resulting suspension for 1 hour, the product was collected by filtration and washed with tert-butyl methyl ether. The solid was dissolved in dichloromethane and 1 N aqueous NaOH solution was added until alkaline. After separation, the aqueous layer was washed with dichloromethane and combined organic layers were dried with sodium sulfate and evaporated. After adding 2-methyltetrahydrofurane and filtration over a Celite pad, the cake was washed with 2-methyltetrahydrofurane and the solvent was evaporated to yield an amber oil (894 g; 89%).

$^1$H NMR (400 MHz, CDCl$_3$): δ ppm 7.33 (d, J=8.8 Hz, 1H); 6.63 (d, J=8.8 Hz, 1H); 4.09 (t, J=5.8 Hz, 2H); 2.83 (t, J=5.8 Hz, 3H); 2.63 (brs, 4H); 2.47 (s, 4H); 2.37-2.45 (in, 2H); 2.25 (s, 3H)

EXAMPLE 6: PREPARATION OF 1-[2-(4-BROMO-2-CHLORO-3-METHYLPHENOXY) ETHYL]-4-METHYLPIPERAZINE AS MONOHYDROCHLORIDE SALT (RING-OPENING OF 1-ALKYL-1-AZONIABICYCLO[2.2.2]OCTANE)

A solution of methyl 4-methylbenzene-1-sulfonate (435 g; 2.34 mol) in anisole (235 mL) was added over 15 minutes to a solution of 1,4-diazabicyclo[2.2.2]octane (286 g; 2.55 mol) in anisole (4.7 L). The white thick suspension was heated to 70° C. for 60 minutes. Cesium carbonate (831 g; 2.55 mol) was added in one portion then a solution or 4-bromo-2-chloro-3-methylphenol (470 g; 2.12 mol), obtained as described in Examples 2 or 3 above, in anisole (470 mL) was added in 12 minutes at 70° C. The brown suspension was heated to 140° C. for 6 hours and the reaction completion was confirmed by HPLC. Water, tert-butyl methyl ether and ethyl acetate were added and the biphasic mixture was stirred for 10 minutes. The layers were separated and then the aqueous phase was extracted with a 1:1 mixture of tert-butyl methyl ether and ethyl acetate. Pooled organic phases were washed with brine then dried over sodium sulfate for about 30 minutes. The suspension was filtered over a Buchner filter and then the cake was washed with tert-butyl methyl ether. The solution of free base was kept aside.

Acetyl chloride (200 g; 2.55 mol) was added to a cooled (0-5° C.) mixture of ethanol (127 g; 2.76 mol) and tert-butyl methyl ether (940 mL) in 35 minutes between 3° C. and 12° C. The solution was stirred for 30 minutes then it was added to the solution of free base in 60 minutes between 20° C. and 25° C. The white suspension was stirred for 60 minutes at 20-25° C. then the solid was collected by filtration over a Buchner filter and the cake was washed twice with tert-butyl methyl ether. The cake was charged back in the flask and triturated in tert-butyl methyl ether for 60 minutes. The suspension was filtered over a Buchner filter and the cake was washed twice with tert-butyl methyl ether. The solid was dried under vacuum at 70-75° C. until constant weight was observed to give the product of the title as an off-white solid (761 g, yield: 93.2%) with a purity of 97.1% by GC-FID.

$^1$H NMR (400 MHz, DMSO-d$_6$): δ ppm 11.10 (brs, 1H); 7.54 (d, J=8.8 Hz, 1H); 7.01 (d, J=9.1 Hz, 1H); 4.27 (brs, 2H); 3.39 (brs, 10H); 2.72 (brs, 3H); 2.44 (s, 3H)

EXAMPLE 7: PREPARATION OF 1-[2-(4-BROMO-2-CHLORO-3-METHYLPHENOXY) ETHYL]-4-METHYLPIPERAZINE AS DIHYDROCHLORIDE SALT

In a 22 L round bottom flask setup in distillation mode, was charged 1-[2-(4-bromo-2-chloro-3-methylphenoxy) ethyl]-4-methylpiperazine, HCl salt (1490 g; 3.88 mol), obtained as described in Example 6 above, and water (14.9 L). Water was partially distilled (2.98 L) to remove residual anisole by azeotrope at 50-55° C. and 40-45 Torr. The solution was cooled to 45° C. then 12 N hydrochloric acid (646 mL; 7.76 mol) was added in 5 minutes. The solution was allowed to cool slowly to 20-25° C. over the week-end. The suspension was then chilled to 0-5° C. and was filtered over a Buchner filter and the flask was rinsed with cold (0-5° C.) water (250 mL). The cake was washed twice with acetone. Solid was charged back in the flask and triturated in acetone for 90 minutes. The suspension was filtered over a Buchner filter and the cake was washed twice with acetone. The solid was dried under vacuum at 75-80° C. for 24 hours to give the product of the title as a white solid (1471 g, yield: 90.2%) with a purity of 99.9% by GC-FID.

$^1$H NMR (400 MHz, DMSO-d$_6$): δ ppm 10.91-13.60 (m, 2H); 7.56 (d, J=8.8 Hz, 1H); 7.03 (d, J=9.1 Hz, 1H); 4.45 (brs, 2H); 3.58 (brs, 10H); 2.79 (brs, 3H); 2.44 (s, 3H)

$^{13}$C NMR (101 MHz, CD$_3$OD), D$_2$O): δ ppm 153.7, 137.9, 132.0, 124.6, 118.0, 113.7, 65.3, 56.9, 51.2, 50.8, 43.7, 20.8

EXAMPLE 8: PREPARATION OF 1-{2-[2-CHLORO-3-METHYL-4-(TETRAMETHYL-1,3,2-DIOXABOROLAN-2-YL)PHENOXY]ETHYL}-4-METHYLPIPERAZINE (BORYLATION REACTION)

1-[2-(4-bromo-2-chloro-3-methylphenoxy)ethyl]-4-methylpiperazine (800.0 g; 2.30 mol), obtained as described in Example 5 (or obtained from transformation of Examples 6 or 7 into freebase), and 2-methyltetrahydrofurane (5.6 L) were charged to a 12 L three-necked round bottom flask under nitrogen. The solution was cooled to between −72° C. and −76° C. using an acetone-dry ice bath. A solution of 2.5M n-butyllithium in hexanes (1196 mL; 2.99 mol) was added over 1.5 hour, keeping the temperature between −62° C. and −74° C. The resulting yellow solution was stirred at between −72° C. and −76° C. for 1 hour. 4,4,5,5-tetramethyl-2-(propan-2-yloxy)-1,3,2-dioxaborolane (556 g; 2.99 mol) was then added over 45 minutes, keeping the reaction mixture between −65° C. and −76° C. The reaction mixture was stirred at a temperature of −65° C. to −76° C. for 1 hour. Reaction completion was observed by HPLC. The reaction mixture was then warned to −25° C. Methanol (200 mL) was then added over 15 minutes. The solution was poured in a solution of ammonium chloride (369 g; 6.90 mol) in water (4 L). The phases were separated. The organic phase was washed with water and then directly evaporated to dryness to give colorless oil. Heptane (2.80 L) was added to dilute the oil at 35-40° C. and crystallization soon occurred. The suspension was stirred for 1 hour at 35-40° C., then cooled to 5° C. for 1 hour. The solids were collected by filtration, then washed with heptanes. The wet cake was dried under high vacuum at 40-50° C. until constant weight to give the product or the title as a white solid (2.200 kg, 85% yield over a total of 3 batches).

$^1$H NMR (400 MHz, CDCl$_3$): δ ppm 7.61 (d, J=8.3 Hz, 1H); 6.72 (d, J=8.3 Hz, 1H); 4.14 (t, J=5.9 Hz, 2H); 2.85 (t, J=5.9 Hz, 2H); 2.64 (brs, 3H); 2.58 (s, 4H); 2.38-2.50 (m, 4H); 2.25 (s, 3H); 1.30 (s, 12H)

EXAMPLE 9: PREPARATION OF 1-{2-[2-CHLORO-3-METHYL-4-(TETRAMETHYL-1,3,2-DIOXABOROLAN-2-YL)PHENOXY]ETHYL}-4-METHYLPIPERAZINE (MIYAURA-TYPE BORYLATION REACTION)

A solution of 1-[2-(4-bromo-2-chloro-3-methylphenoxy)ethyl]-4-methylpiperazine (20.1 g; 58 mmol), obtained as described in Example 5 (or obtained from transformation of Examples 6 or 7 into freebase), in 1,4-dioxane (200 mL) was degassed with nitrogen during 20 minutes. Potassium acetate (19.3 g; 197 mmol) and 4,4,4',4',5,5,5',5'-octamethyl-2,2'-bi-1,3,2-dioxaborolane (17.8 g; 70 mmol) were added and the suspension was degassed again for 20 minutes. Pd(PPh$_3$)$_2$Cl$_2$ (814 mg; 1.16 mmol) was added and the suspension was heated to 100° C. for two hours. Reaction completion was confirmed by HPLC. The suspension was cooled to 20-25° C. and toluene (100 mL) was added. The suspension was filtered over Celite (15 g) and the cake was rinsed with toluene (40 mL). Activated charcoal (4.0 g) was added to the solution and stirred for 1 hour. The suspension was filtered over Celite (15 g) and silica gel (15 g) then the cake was rinsed with toluene (40 mL). The solution was concentrated to dryness, heptane (100 mL) was added, concentrated to dryness and this operation was repeated once more. The residue was dissolved in heptane (150 mL) and treated with activated charcoal (4.0 g) for 60 minutes. The suspension was filtered over Celite (15 g) and the cake was rinsed twice with heptane (2×20 mL). The solution was concentrated to dryness, heptane (40 mL) was added to the residue and the product was crystallized at 20-25° C. over four hours. The suspension was cooled to 0-5° C. for one hour and the product was collected by filtration. The cake was washed with cold (0-5° C.) heptane (20 mL) and the solid was dried at 35-40° C. until constant weight to afford 10.1 g of product as a white solid. Mother liquors were concentrated to dryness then heptane (20 mL) was added to the residue and the product was crystallized at 20-25° C. over four hours. The suspension was cooled to 0-5° C. over one hour and the product was collected by filtration. The cake was washed with cold (0-5° C.) heptane (10 mL) then the solid was dried at 35-40° C. until constant weight to afford 5.6 g of product as a white solid. Two crops were combined to give a total of 15.7 g (69% yield).

$^1$H NMR (400 MHz, CDCl$_3$): δ ppm 7.64 (d, J=8.3 Hz, 1H); 6.76 (d, J=8.3 Hz, 1H); 4.18 (t, J=5.8 Hz, 2H); 2.88 (t, J=5.9 Hz, 2H); 2.25-2.83 (m, 14H); 1.34 (s, 12H)

EXAMPLE 10: PREPARATION OF 1-{2-[2-CHLORO-3-METHYL-4-(TETRAMETHYL-1,3,2-DIOXABOROLAN-2-YL)PHENOXY]ETHYL}-4-METHYLPIPERAZINE (MIYAURA-TYPE BORYLATION REACTION)

In a solution of 1-[2-(4-bromo-2-chloro-3-methylphenoxy)ethyl]-4-methylpiperazine dihydrochloride salt (1000 g; 1 eq.; obtained as described in Example 7) in ethyl acetate (10 vol.), 4,4,4',4',5,5,5',5'-octamethyl-2,2'-bi-1,3,2-dioxaborolane (784 g; 1.3 eq.), potassium acetate (1284 g; 5.5 eq.) and Pd(PPh$_3$)$_2$Cl$_2$ (50 g; 0.03 eq.) were added under nitrogen. Under stirring, the suspension was heated to reflux for 16 hours. After cooling to 20° C., the reaction mixture is then filtrated and cake was washed with ethyl acetate (1.5 vol.). The organic layer is then washed with L-acetyl-cysteine aqueous solution at 5%, buffered at pH 7 with AcOK (10 vol.). After layers separation, organic layer was concentrated at 2 volumes and then proceeded to a solvent switch toward acetonitrile at 30° C. under vacuum. The temperature was then decreased to −10° C. and crystallization occurred. After filtration, the solid was dried at 40° C. to afford the product of the title as a white solid (48% yield).

$^1$H NMR (400 MHz, CDCl$_3$): δ ppm 7.64 (d, J=8.3 Hz, 1H); 6.76 (d, J=8.3 Hz, 1H); 4.18 (t, J=5.8 Hz, 2H); 2.88 (t, J=5.9 Hz, 2H); 2.25-2.83 (m, 14H); 1.34 (s, 12H)

EXAMPLE 11: PREPARATION OF 4-BROMO-2-CHLORO-3-METHYLPHENOL IN LARGE SCALE (ONE-POT HYDROXYLATION AND REGIOSELECTIVE MONOBROMINATION REACTIONS)

In a reactor, water (390 L, 6.0 vol.) and potassium hydroxide (52.2 Kg, 790.8 mol) was added and dissolved. When the heat of dissolution was subsided, 1,4-dioxane (130 L, 2 vol.) and 3-bromo-2-chlorotoluene (65 Kg, 316.3 mol) was charged then, the solution was degassed, under stirring, with nitrogen for 30 minutes. t-BuXphos (5.38 Kg, 12.65 mol) and Pd$_2$(dba)$_3$ (2.90 Kg, 3.16 mol) were added and the suspension was heated to reflux for 90 minutes. Reaction completion was confirmed by GC then the reaction mixture was cooled to 20~25° C. t-Butylmethyl ether (146 L) was added and the biphasic mixture was stirred for 20 minutes. The reaction mixture was filtered over a Celite pad, the filter cake was rinsed with t-butylmethyl ether (39 L, 0.6 vol.) and 1 N potassium hydroxide solution (78 L, 1.2 vol.) then the phases were separated. The aqueous phase was washed three times with t-butylmethyl ether (3×110.5 L, 3×1.7 vol.) then was acidified to pH 1~2 with 12 N hydrochloric acid under 25~30° C. The solution was extracted three times with dichloromethane (1×110.5 L, 1.7 vol. and 2×42.3 L, 2×0.65 vol.). The combined organic layer was transferred to a reactor.

Acetic acid (107.3 L, 1.65 vol.) was added to the solution of 2-chloro-3-methylphenol. The solution was cooled to −10~−5° C. under nitrogen and a solution of bromine (51.1 Kg, 319.5 mol) in dichloromethane (88 L, 1.35 vol.) was added for 1.5 hours between −10° C. and −2° C. Water (260 L, 4.0 vol.) was added and the mixture was warmed to 20~25° C. Sodium bisulfate (9.9 Kg, 94.9 mol) was added then the solution was stirred for 20 minutes. Phase was splitted then the aqueous phase extracted with dichloromethane. The combined organic phases were washed twice with water, twice with 10% potassium bicarbonate solution and 20% sodium chloride solution. The solution was dried over magnesium sulfate then filtered and the cake was washed with dichloromethane. The solvents were removed by vacuum distillation. The residual 1,4-dioxane was azeotroped with heptane to give 70.1 Kg of product of the title. (crude yield: 100.1%)

$^1$H NMR (600 MHz, CDCl$_3$): 2.50 (s, 3H), 5.57 (s, 1H), 6.78 (d, 1H), 7.35 (d, 1H)

EXAMPLE 12: PREPARATION OF 1-[2-(4-BROMO-2-CHLORO-3-METHYLPHENOXY)ETHYL]-4-METHYLPIPERAZINE MONOHYDROCHLORIDE IN LARGE SCALE (RING-OPENING OF 1-ALKYL-1-AZONIABICYCLO[2.2.2]OCTANE)

In a reactor, was charged anisole (701 L, 10.0 vol.) and 1,4-diazabicyclo[2.2.2]octane (42.6 Kg, 379.6 mol) and stirred under nitrogen. Methyl p-toluenesulfonate (64.8 Kg, 348.0 mol) was added by portions. The reaction mixture was heated to 70° C. for 1 hour. Cesium carbonate (123.7 Kg, 379.6 mol) was added in one portion then a solution of 4-bromo-2-chloro-3-methylphenol (70.1 Kg, 316.33 mol; obtained as described in Example 11) in anisole (50 Kg) was added at 70° C. The brown solution was heated to 140° C. for 6 hours and the reaction completion was confirmed by GC. After the reaction mixture was cooled to room temperature, water, t-butylmethyl ether and ethyl acetate were added and the biphasic solution was stirred for 10 minutes. The layers were separated and the organic phases were washed with 20% sodium chloride aqueous solution then dried over magnesium sulfate. The suspension was filtered over a Buchner filter and then the cake was washed with t-butylmethyl ether. The solution of free base was charged in a reactor and kept aside for later.

In a reactor, t-butylmethyl ether (140.2 L, 2.0 vol.) and ethanol (19.0 Kg, 412.4 mol) was charged and cooled to 0~5° C. Acetyl chloride (29.8 Kg, 379.6 mol) was added under 10~15° C. The solution was stirred for 30 minutes then it was added to the solution of free base between 15° C. and 25° C. The white suspension was stirred for 60 minutes at 20~25° C. then filtered with Buchner filter and the cake was washed with t-butylmethyl ether.

The filter cake and t-butylmethyl ether were charged back in the reactor and stirred for 60 minutes. The suspension was filtered over a Buchner filter and the cake was washed with t-butylmethyl ether. The solid was dried under vacuum at 70~75° C. for 16 hours to give the product of the title as an white solid (101 Kg, yield: 83.1%)

$^1$H NMR (600 MHz, DMSO-$d_6$): 2.42 (s, 3H), 2.70 (s, 3H), 2.8-3.8 (br, 10H), 4.25 (br, 2H), 6.95 (d, 1H), 7.52 (d, 1H)

EXAMPLE 13: PREPARATION OF 1-[2-(4-BROMO-2-CHLORO-3-METHYLPHENOXY)ETHYL]-4-METHYLPIPERAZINE DIHYDROCHLORIDE IN LARGE SCALE

In a reactor, was charged water (1010 L, 10 vol.) and 1-[2-(4-Bromo-2-chloro-3-methylphenoxy)ethyl]-4-methylpiperazine monohydrochloride (101 Kg, 262.9 mol; obtained as described in Example 12). Water was partially distilled to remove residual anisole by azeotrope at 45~50° C. and 55~60 Torr. 12 N Hydrochloric acid (43.8 L, 525.8 mol) was added to the aqueous solution at 45° C. The solution was cooled slowly to 15~20° C. during 3 hours and stirred additionally for 12 hours. The suspension was filtered over Buchner filter and the cake was washed with cold water (17 L, 0.17 vol.) and acetone (200 L, 2 vol.). The solid was charged back to the reactor then acetone was added and the suspension was stirred for 60 minutes and filtered with Buchner filter. The filter cake was washed with acetone and dried under vacuum at 75~80° C. for 24 hours to give the product of the title (99.5 Kg, 90.0%) as a white solid with a purity of 99.4% by GC-FID $^1$H NMR (600 MHz, DMSO-$d_6$): 2.43 (s, 3H), 2.78 (s, 3H), 3.2-3.9 (br, 10H), 4.47 (br, 2H), 7.02 (d, 1H), 7.56 (d, 1H)

The invention claimed is:

1. A process for preparing a compound of formula (I):

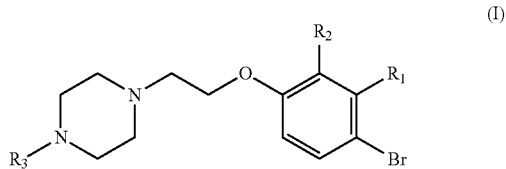

wherein:
 $R_1$ and $R_2$, independently of one another, represent a halogen atom, a linear or branched $(C_1\text{-}C_6)$alkyl group, a linear or branched $(C_1\text{-}C_6)$alkoxy group, a linear or branched $(C_1\text{-}C_6)$alkoxy$(C_1\text{-}C_6)$alkoxy group, a hydroxyl group or a cyano group, and
 $R_3$ represents a linear or branched $(C_1\text{-}C_6)$alkyl group,
comprising the step of reacting a compound of formula (IV):

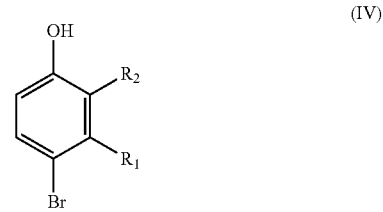

with a compound of formula (V):

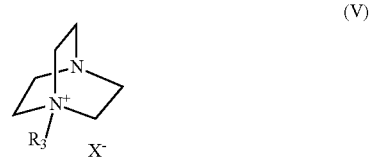

wherein X$^-$ represents a monovalent anionic counter-ion, in a solvent, at high temperature in the presence of a base to yield the compound of formula (I).

2. The process according to claim 1, wherein the solvent is polar aprotic.

3. The process according to claim 1, wherein the temperature is above 135° C.

4. The process according to claim 1, wherein the base is a carbonate salt.

5. The process according to claim 1, wherein the compound of formula (I) is isolated as a monohydrohalide salt or a dihydrohalide salt.

6. The process according to claim 1, wherein 1,4-diazabicyclo[2.2.2]octane is employed in the process to obtain the compound of formula (V).

7. The process according to claim 1, wherein 1,4-diazabicyclo[2.2.2]octane is employed in the process to obtain the compound of formula (I).

8. The process according to claim 1, wherein the compound of formula (IV):

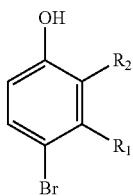

(IV)

wherein $R_1$ and $R_2$, independently of one another, represent a halogen atom, a linear or branched $(C_1\text{-}C_6)$alkyl group, a linear or branched $(C_1\text{-}C_6)$alkoxy group, a linear or branched $(C_1\text{-}C_6)$alkoxy$(C_1\text{-}C_6)$alkoxy group, a hydroxyl group or a cyano group, is obtained by a regioselective monobromination reaction of a compound of formula (VI):

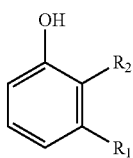

(VI)

in a solvent in the presence of a brominating agent selected from bromine, sodium bromide/trichloroisocyanuric acid and bromine/sodium acetate.

9. The process according to claim 8, wherein the reaction is carried out in the presence of 1 equivalent of brominating agent.

10. The process according to claim 8, wherein the brominating agent is bromine.

11. The process according to claim 8, wherein the solvent is selected from acetic acid, dichloromethane, a mixture of methanol and sulfuric acid, and a mixture of acetic acid and dichloromethane.

12. The process according to claim 8, wherein the reaction is carried out by diluting the compound of formula (VI) with about 10 to about 20 volumes of organic solvents or mixture of organic solvents.

13. The process according to claim 8, wherein the compound of formula (VI):

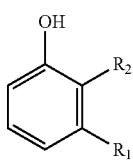

(VI)

wherein $R_1$ and $R_2$, independently of one another, represent a halogen atom, a linear or branched $(C_1\text{-}C_6)$alkyl group, a linear or branched $(C_1\text{-}C_6)$alkoxy group, a linear or branched $(C_1\text{-}C_6)$alkoxy$(C_1\text{-}C_6)$alkoxy group, a hydroxyl group or a cyano group, is obtained by a hydroxylation reaction of a compound of formula (VII):

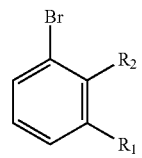

(VII)

in a solvent in the presence of a metal transition complex and a base.

14. The process according to claim 13, wherein the metal transition complex is a palladium complex comprising a palladium catalyst and a ligand.

15. The process according to claim 14, wherein the reaction is carried out in the presence of at least 0.01 equivalent of palladium catalyst.

16. The process according to claim 14, wherein the reaction is carried out in the presence of at least 0.03 equivalent of ligand.

17. The process according to claim 13, wherein the base is a hydroxide salt.

18. The process according to claim 13, wherein the solvent is 1,4-dioxane or a mixture of water and 1,4-dioxane.

19. The process according to claim 13, wherein conversion of the compound of formula (VII) into the compound of formula (IV) is carried out directly without isolating compound of formula (VI).

20. A process for preparing a compound of formula (II):

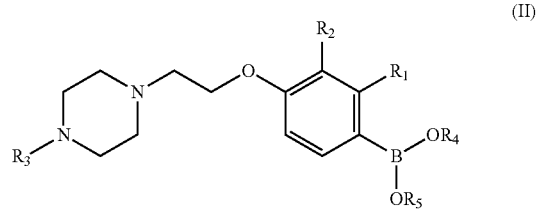

(II)

wherein:
$R_1$ and $R_2$, independently of one another, represent a halogen atom, a linear or branched $(C_1\text{-}C_6)$alkyl group, a linear or branched $(C_1\text{-}C_6)$alkoxy group, a linear or branched $(C_1\text{-}C_6)$alkoxy$(C_1\text{-}C_6)$alkoxy group, a hydroxyl group or a cyano group,
$R_3$ represents a linear or branched $(C_1\text{-}C_6)$alkyl group, and
$R_4$ and $R_5$ represent a hydrogen, a linear or branched $(C_1\text{-}C_6)$alkyl group, or $R_4$ and $R_5$, together with the oxygen atoms carrying them, form a ring which may be substituted by one to four linear or branched $(C_1\text{-}C_6)$alkyl group,
comprising the step of reacting a compound of formula (I), which compound of formula (I) is obtained by the process according to claim 1:

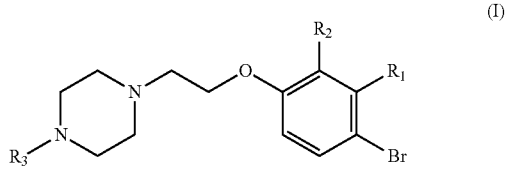

(I)

with a boronic ester of formula (VIII):

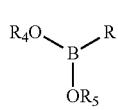
(VIII)

wherein R represents a hydrogen atom, a hydroxy group, a linear or branched ($C_1$-$C_6$)alkoxy group, or a ($C_0$-$C_6$) alkyl-B(OR$_4$)(OR$_5$) group to yield the compound of formula (II).

21. The process according to claim 20, wherein the reaction consists of the action of the compound of formula (VIII), wherein R represents a hydrogen atom, a hydroxy group, or a linear or branched ($C_1$-$C_6$)alkoxy group, in an organic solvent or a mixture of organic solvents in the presence of a base.

22. The process according to claim 20, wherein the reaction consists of the action of the compound of formula (VIII), wherein R represents a ($C_0$-$C_6$)alkyl-B(OR$_4$)(OR$_5$) group, in an organic solvent or a mixture of organic solvents in the presence of a base and a palladium complex.

23. A process for preparing a compound of formula (II):

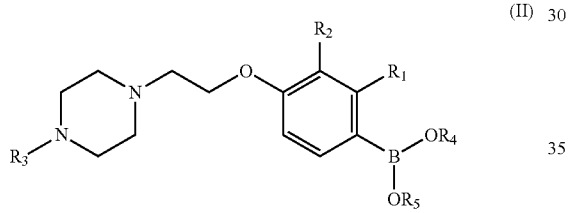
(II)

wherein:
  $R_1$ and $R_2$, independently of one another, represent a halogen atom, a linear or branched ($C_1$-$C_6$)alkyl group, a linear or branched ($C_1$-$C_6$)alkoxy group, a linear or branched ($C_1$-$C_6$)alkoxy($C_1$-$C_6$)alkoxy group, a hydroxyl group or a cyano group,
  $R_3$ represents a linear or branched ($C_1$-$C_6$)alkyl group, and
  $R_4$ and $R_5$ represent a hydrogen, a linear or branched ($C_1$-$C_6$)alkyl group, or $R_4$ and $R_5$ form with the oxygen atoms carrying them a ring which may be substituted by one to four linear or branched ($C_1$-$C_6$)alkyl group,
wherein a compound of formula (VII):

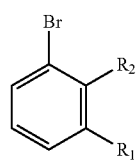
(VII)

is subjected to a hydroxylation reaction in the presence of a metal transition complex and a base in a solvent, to yield a compound of formula (VI):

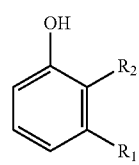
(VI)

which compound of formula (VI) is subjected to a regioselective monobromination reaction, in the presence of a brominating agent in a solvent, to yield a compound of formula (IV):

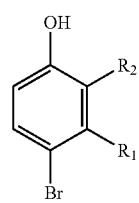
(IV)

which compound of formula (IV) is reacted in a solvent at high temperature in the presence of a base and a compound of formula (V):

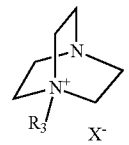
(V)

wherein X$^-$ represents a monovalent anionic counter-ion, to yield a compound of formula (I):

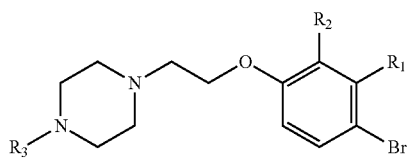
(I)

which compound of formula (I) undergoes a borylation reaction in the presence of a boronic ester of formula (VIII):

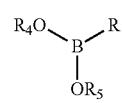
(VIII)

wherein R represents a hydrogen atom, a hydroxy group, a linear or branched ($C_1$-$C_6$)alkoxy group, or a ($C_0$-$C_6$) alkyl-B(OR$_4$)(OR$_5$) group, to yield the compound of formula (II).

24. The process according to claim 20, wherein $R_1$ represents a linear or branched $(C_1-C_6)$alkyl group, $R_2$ represents a halogen atom and $R_3$ represents a methyl group.

25. The process according to claim 2, wherein $R_1$ and $R_3$ represent a methyl group and $R_2$ represents a chlorine atom.

26. The process according to claim 25, which further comprises converting the compound of formula (II) to 2-{[5-{3-chloro-2-methyl-4-[2-(4-methylpiperazin-1-yl)ethyoxy]phenyl}-6-(5-fluorofuran-2-yl)thieno[2,3-d]pyrimidin-4-yl]oxy}-3-(2-{[1-(2,2,2-trifluoroethyl)-1H-pyrazol-5-yl]methoxy}phenyl)propanoic acid or 2-{[5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid.

27. The process according to claim 5, wherein 1,4-diazabicyclo[2.2.2]octane is employed in the process to obtain the compound of formula (II), and wherein the process further comprises converting the compound of formula (II) to 2-{[5-{3-chloro-2methyl-4-[2-(4-methylpiperazin-1-yl)ethoxy]phenyl}-6(5-fluorofuran-2-yl)thieno[2,3-d]pyrimidin-4-yl]oxy}-3-(2-{[1-(2,2,2-trifluoroethyl)-1H-pyrazol-5-yl]methoxy}phenyl)propanoic acid or 2-{[5-{3-chloro-2-methyl-4-[2-(4-methylpiperazin-1-yl)ethoxy]phenyl}-6-(4fluorophenyl)thieno[2,3-d]pyrimidin-4-yl]oxy}-3-(2-{[2-(2-methoxyphenyl)pyrimidin-4-yl]methoxy}phenyl)propanoic acid.

\* \* \* \* \*

UNITED STATES PATENT AND TRADEMARK OFFICE
CERTIFICATE OF CORRECTION

PATENT NO. : 11,512,062 B2
APPLICATION NO. : 17/283107
DATED : November 29, 2022
INVENTOR(S) : Beauregard et al.

It is certified that error appears in the above-identified patent and that said Letters Patent is hereby corrected as shown below:

On the Title Page

Column 2:
Item (56) Under "FOREIGN PATENT DOCUMENTS": The first reference date should be
-- 6/2015 --.

Signed and Sealed this
Twenty-eighth Day of February, 2023

Katherine Kelly Vidal
*Director of the United States Patent and Trademark Office*